US012802806B2

(12) United States Patent
Dong et al.

(10) Patent No.: US 12,802,806 B2
(45) Date of Patent: Nov. 17, 2026

(54) INSTRUMENT HEALTH DATA WORKFLOW

(71) Applicants: Dionex Corporation, Sunnyvale, CA (US); Thermo Electron North America LLC, West Palm Beach, FL (US)

(72) Inventors: Yubo Dong, Fremont, CA (US); Rajesh Raina, Milpitas, CA (US); Sachin Burange, Milpitas, CA (US); Ron Baron, San Jose, CA (US); Shan Randall, Beaverton, OR (US)

(73) Assignees: Dionex Corporation, Sunnyvale, CA (US); Thermo Electron North America LLC, West Palm Beach, FL (US)

( * ) Notice: Subject to any disclaimer, the term of this patent is extended or adjusted under 35 U.S.C. 154(b) by 21 days.

(21) Appl. No.: 18/948,919

(22) Filed: Nov. 15, 2024

(65) Prior Publication Data

US 2026/0142023 A1 May 21, 2026

(51) Int. Cl.
*G16H 40/40* (2018.01)

(52) U.S. Cl.
CPC .................................. *G16H 40/40* (2018.01)

(58) Field of Classification Search
CPC ...................................................... G16H 40/40
See application file for complete search history.

(56) References Cited

U.S. PATENT DOCUMENTS

2004/0153823 A1* 8/2004 Ansari ................ G06F 11/0793 714/38.14
2012/0158633 A1* 6/2012 Eder ...................... G16H 50/50 707/E17.014
2021/0064016 A1 3/2021 Manturana
2023/0229458 A1 7/2023 Andrews et al.
(Continued)

FOREIGN PATENT DOCUMENTS

WO 2024258732 A2 12/2024

OTHER PUBLICATIONS

Wikipedia "webhook" page explain the meaning of webhooking, retrieved from: https://en.wikipedia.org/wiki/Webhook (Year: 2025).*
(Continued)

*Primary Examiner* — Yair Leibovich
(74) *Attorney, Agent, or Firm* — Michael Best & Friedrich LLP

(57) ABSTRACT

The present disclosure provides a scientific instrument support apparatus comprising a first logic, a second logic, and a third logic. The first logic subscribes to events from a device driver, receives signature data events including a generated signature event, generates signature data with a specified signature identifier in response to the generated signature event, and transmits the signature data to the second logic. The second logic receives the signature data from the first logic, processes the signature data, writes the processed signature data to an instrument health database, and transmits the signature data to a cloud-based database. The third logic presents a graphical user interface based on
(Continued)

the processed signature data. The apparatus enables efficient collection, processing, and presentation of scientific instrument data for improved monitoring and analysis.

20 Claims, 14 Drawing Sheets

(56) References Cited

U.S. PATENT DOCUMENTS

| | | | |
|---|---|---|---|
| 2024/0053741 | A1 | 2/2024 | Amaro, Jr. et al. |
| 2024/0386074 | A1 | 11/2024 | Ressler et al. |

OTHER PUBLICATIONS

DBewaver products "Microsoft SQL server" in support of SQL includes driver, retrieved from : https://dbeaver.com/docs/dbeaver/Database-driver-Microsoft-SQL-Server/#:~:text=DBeaver%20interacts%20with%20the%20SQL,database%20window%20for%20these%20extensions (Year: 2025).*

Oracle: "Creating and Saving manifest file", in support of SQL Oracle™ relational database works with manifest file, retrieved from : https://docs.oracle.com/en/cloud/saas/enterprise-performance-management-common/svimb/creating_saving_manifest_108x259f75ca.html (Year: 2025).*

Oracle: "Oracle Cloud Infrastructure Documentation", in support of SQL Oracle™ relational database works Rest API.retrieved from : https://docs.oracle.com/en-us/iaas/Content/data-integration/using/createda-rest.htm#:~:text=Currently%2C%20you%20have%20to%20upload,myapi.example.com/v1 (Year: 2025).*

Tigerdata: SQL/JSON Data Model in support of SQL contains JSON, retrieved from : https://www.tigerdata.com/learn/sql-json-data-model-and-json-in-sql-a-postgresql-perspective (Year: 2025).*

European Patent Office. Extended European Search Report for Application No. 25212761.8, dated Apr. 2, 2026 (12 pages).

* cited by examiner

Device Declaration Signature
Displays instrument (Mass Spectrometer) and all sub-devices (configuration) all with unique identifiers (@id)

400

```
"facet" : [
  {
    "@type": "adapt:Declaration",
    "startTime": "2024-03-15T17:26:56.366464+01:00",
    "endTime": "2024-03-15T17:27:01.4153261+01:00",
    "declarationOf": [
      {
        "@id": "urn:uuid:b93f56a0-45d3-563d-bbc8-306cd94b9b61",
        "@type": "adapt-entities:Exploris_Merkur_A",
        "serialNumber": "MM10004C",
        "deviceKey": "Exploris-Exploris_240-MM10004C",
        "components": [
            "urn:uuid:8cffffd1-faf3-52a0-8f1d-b5c6317de1d7",
            "urn:uuid:5387340f-e1dc-5acb-85a9-7eda980abedd",
            "urn:uuid:4afc6528-04ae-53e8-8123-86afdcd56f29",
            "urn:uuid:ae2824e1-0f05-5cda-ba4e-6c8e45b70d36",
            "urn:uuid:bbb779a7-456d-53df-af8c-a780207c0152",
            "urn:uuid:3f8f15d7-4f21-51cd-9a5b-9a82454111a6",
            "urn:uuid:f4faf957-0fc3-5968-b48e-4c303e5f7c23",
            "urn:uuid:2f070e11-0af6-54e2-9d58-2c649b19a6d6",
            "urn:uuid:daa4b568-f9e8-56d1-bdba-9ec1487b244b",
            "urn:uuid:46c5df3f-8834-5c44-9bab-e8f39d257723",
            "urn:uuid:b6755aef-3c3c-5ff1-bc41-8cf75d01e84c"
        ]
      },
      {
        "@id": "urn:uuid:b6755aef-3c3c-5ff1-bc41-8cf75d01e84c",
        "@type": "adapt-entities:Exploris_TurboPump",
        "deviceKey": "Exploris-Exploris_240-MM10004C"
      },
      {
        "@id": "urn:uuid:46c5df3f-8834-5c44-9bab-e8f39d257723",
        "@type": "adapt-entities:Exploris_TurboPump",
        "deviceKey": "Exploris-Exploris_240-MM10004C"
      },
      {
```

FIG. 4A

```
"@id": "urn:uuid: daa4b568-f9e8-56d1-bdba-9ec1487b244b",
"@type": "adapt-entities:Exploris_TurboPump",
"deviceKey": "Exploris-Exploris_240-MM10004C"
},
{
"@id": "urn:uuid:2f070e11-0af6-54e2-9d58-2c649b19a6d6",
"@type": "adapt-entities:Exploris_SyringePump",
"deviceKey": "Exploris-Exploris_240-MM10004C"
},
{
"@id": "urn:uuid:f4faf957-0fc3-5968-b48e-4c303e5f7c23",
"@type": "adapt-entities:Exploris_Orbitrap",
"deviceKey": "Exploris-Exploris_240-MM10004C"
},
{
"@id": "urn:uuid:3f8f15d7-4f21-51cd-9a5b-9a82454111a6",
"@type": "adapt-entities:Exploris_IonTrapping",
"deviceKey": "Exploris-Exploris_240-MM10004C"
},
{
"@id": "urn:uuid:bbb779a7-456d-53df-af8c-a780207c0152",
"@type": "adapt-entities:Exploris_IonTransfer-FU",
"deviceKey": "Exploris-Exploris_240-MM10004C"
},
{
"@id": "urn:uuid:ae2824e1-0f05-5cda-ba4e-6c8e45b70d36",
"@type": "adapt-entities:Exploris_IonSourceInterface-LC",
"devicKey": "Exploris-Exploris_240-MM10004c"
},
{
"@id": "urn:uuid:4afc6528-04ae-53e8-8123-86afdcd56f29",
"@type": "adapt-entities:Exploris_ESISource",
"deviceKey": "Exploris-Exploris_240-MM10004C"
},
{
"@id": "urn:uuid:5387340f-e1dc-5acb-85a9-7eda980abedd",
"@type": "adapt-entities:Exploris_DARTSource",
"deviceKey": "Exploris-Exploris_240-MM10004C"
```

FIG. 4B

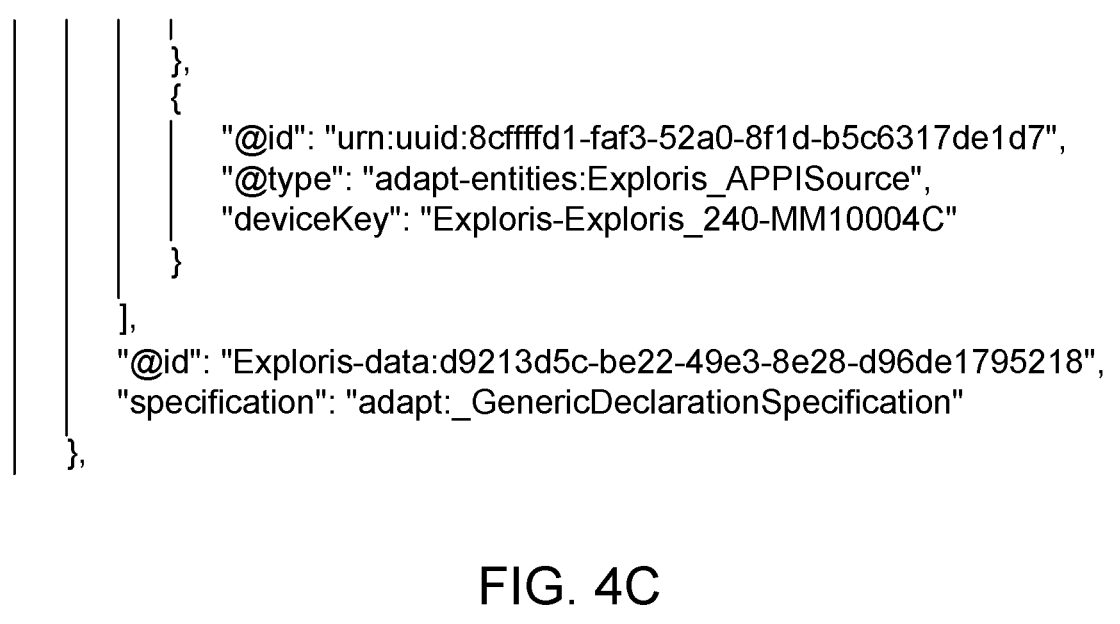

```
      },
      {
        "@id": "urn:uuid:8cffffd1-faf3-52a0-8f1d-b5c6317de1d7",
        "@type": "adapt-entities:Exploris_APPISource",
        "deviceKey": "Exploris-Exploris_240-MM10004C"
      }
    ],
    "@id": "Exploris-data:d9213d5c-be22-49e3-8e28-d96de1795218",
    "specification": "adapt:_GenericDeclarationSpecification"
  },
```

FIG. 4C

402

State signature change from "Ready" to "Running"

```
{
    "@type": "adapt: StateChange",
    "isAbout": "urn: uuid: a29fcfa5-86e8-5474-90d2-0a94c73b90ca",
    "fromState": "adapt-t:_Ready",
    "toState": "adapt-t:_Running",
    "@id": "Tribrid-data:1f5c29db-655f-41de-9da7-2aa6eddf3fa4",
    "startTime": "2024-06-24T11:13:01-07:00",
    "endTime": "2024-06-24T11:13:01-07:00",
    "specification": "Tribrid-spec: _stateChange_to_running"
}
]
```

FIG. 4D

404

Observation signature (read back aggregation) vacuum min/max/mean over 24 hours

```
},
{
    "@type": "adapt:Observation",
    "isAbout": "urn:uuid:f4faf957-0fc3-5968-b48e-4c303e5f7c23",
    "payload": {
        "@type": "rdf:JSON"
        "@value": "{\"min\":3.5E-11,\"max\":4.1E-11,\"mean\":3.822469485229005E-11,
        \"standardDeviation\":6.765110385803138E-13}"
    },
    "@id": "Tribrid-data:f1e257db-3da1-43bb-a920-6f18b4bf5734",
    "startTime": "2024-06-23T00:00:00-07:00",
    "endTime": "2024-06-24T00:00:00-07:00",
    "specification": "Tribrid-spec:_observation_UHVPressure-24hr"
},
{
```

FIG. 4E

406

Usage signature spent 82,800 seconds with HESI (heated electrospray ionization) source

```
},
{
    "@type": "adapt:Usage",
    "isAbout": "urn:uuid:05fd6a31-2238-5865-b279-a59e65ae2929",
    "payload": {
        "@type": "rdf:JSON",
        "@value": "{\"count\":82800}"
    },
    "@id": "Tribrid-data:8f3b21e0-4855-47d5-8e6d-b9eaeebdd714",
    "startTime": "2024-06-23T00:00:00-07:00",
    "endTime": "2024-06-24T00:00:00-07:00",
    "specification": "Tribrid-spec:_usage_Time Spent With HESI Source"
},
```

FIG. 4F

INSTRUMENT HEALTH DATA WORKFLOW

BACKGROUND

Scientific instruments may include a complex arrangement of movable components, sensors, input and output ports, energy sources, and consumable components. Failures or changes in any part of this arrangement may result in a "downed" instrument, one that is not able to perform its intended function. Scientific instruments include data, which can be extracted or transmitted for monitoring the health of the instruments.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, not by way of limitation, in the figures of the accompanying drawings.

FIGS. 4A-4F illustrate example data structures implemented within the scientific instrument support system of FIGS. 2A and 2B, in accordance with various embodiments.

DETAILED DESCRIPTION

Figure 1:
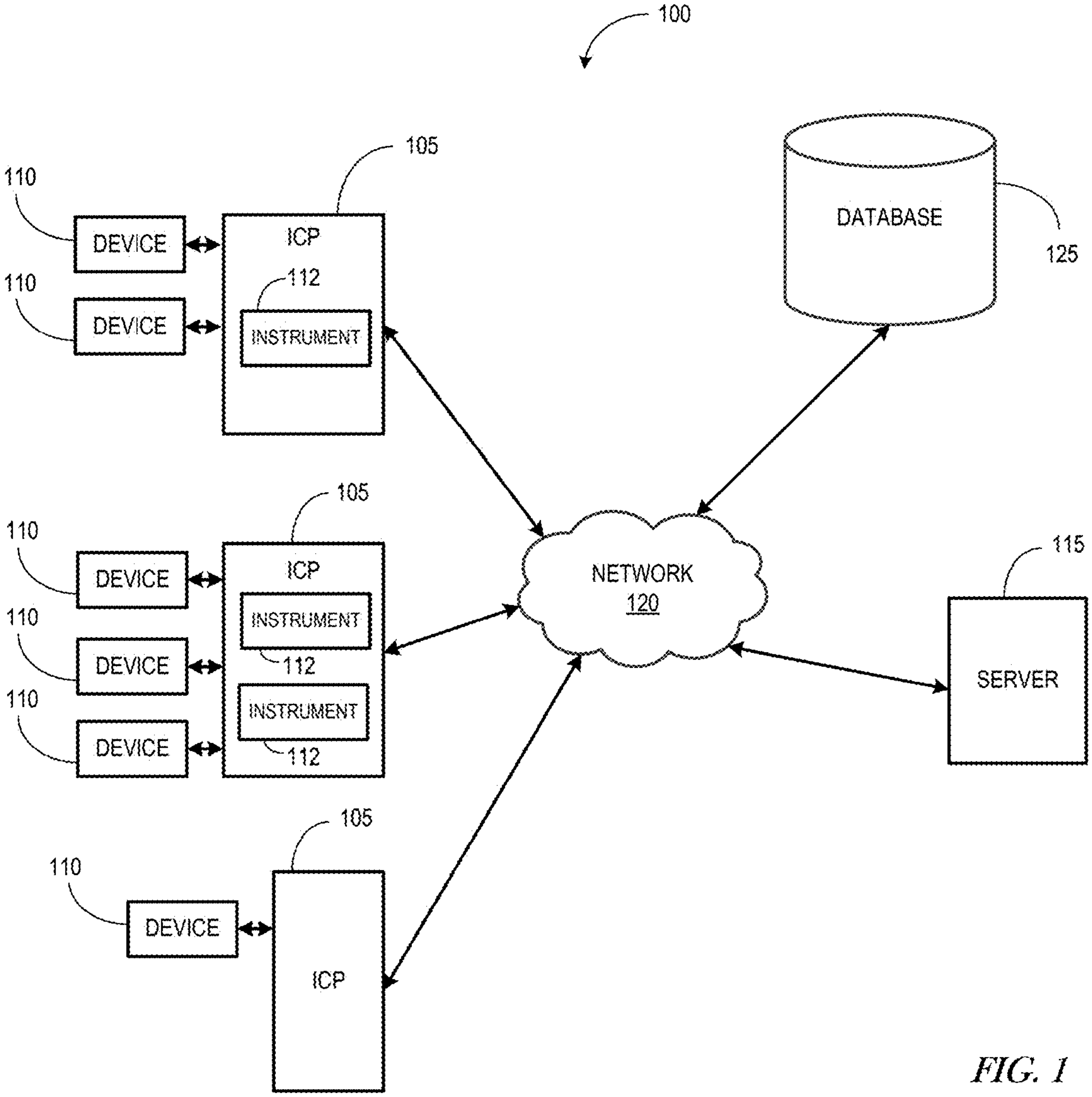
FIG. 1 is a block diagram of an example scientific instrument support system in which some or all of the scientific instrument support methods disclosed herein may be performed, in accordance with various embodiments.

Modern laboratory systems include a significant number of medical and research devices and instruments across large facilities. Additionally, during research and use of the instruments, users in one facility may utilize a device or instrument in another facility connected via a wired or wireless communication network (for example, via the cloud). While these technological advances have allowed for improved interconnectivity and new means of conducting research, the broad portfolio of instruments has varied amounts and types of configuration and health data, making it difficult to monitor the health of the laboratory systems effectively. Instruments of different classes or form different manufacturer may generate, store, and transmit data differently. In addition, each device may have a data manifest including tens of thousands of attributes. As a consequence, operators of such systems lack a single platform to monitor their systems for health and performance.

Accordingly, embodiments described herein provide systems, methods, and apparatuses for instrument health data workflow. Embodiments presented herein provide structured, standardized data across multiple instruments over time. Using such embodiments, operators of scientific instruments can implement a unified framework with a complete end-to-end workflow of instrument of health data from definition, generation, transportation, processing, storage, and utilization. Using embodiments provided herein, device drivers collect data manifests, which are processed using specifications and schema to produce signature data in a single format, which can be saved locally, stored in a cloud, or used to provide comprehensive instrument health data to operators using a web-based application.

An operator may wish to see a view of the health of all devices provided in the research system. Embodiments described herein provide a user interface providing a summarized view of devices with the research system. Devices and their statuses may be represented on the user interface by various shapes, icons, colors, patterns, and the like. An operator may interact with the devices using the user interface to view additional details of the device and adjust characteristics of the device.

Disclosed herein are scientific instrument support systems, as well as related methods, computing devices, and computer-readable media.

In some aspects, the techniques described herein relate to a scientific instrument support apparatus, including: a first logic to: subscribe to events from a device driver; receive from the device driver, signature data events based on the event subscriptions, the signature data events including a generated signature event; and responsive to receiving the generate signature event, generate a signature data with a specified signature identifier; and transmit the signature data to a second logic; a second logic to: receive the signature data from the first logic; process the signature data; write the processed signature data to an instrument health database; and transmit the signature data to a cloud-based database; and a third logic to present a graphical user interface based on the processed signature data.

In some aspects, the techniques described herein relate to a method for scientific instrument support, including: receiving, with a driver module, a subscription request including a device identifier and a signature identifier; sending, to a data performance metrics module, a data manifest based on the device identifier and the signature identifier; generating, by the data performance metrics module, a signature data based on the data manifest and a specification file identified by the signature identifier; transmitting with the data performance metrics module the signature data to the driver module; and transmitting, to an instrument listening service, the processed signature data.

The scientific instrument support embodiments disclosed herein may achieve improved performance relative to conventional approaches. Embodiments presented herein can provide longitudinal data for "healthy" systems, and objective data to different consumers. A consistent data framework allows operators to query the database for concise reporting of recent events and provide self-recovery. This leads to reduced downtime, service call avoidance, and more consistent system performance. Furthermore, a reliable data workflow improves product development/improvement and efficiency. The embodiments disclosed herein thus provide improvements to scientific instrument technology (e.g., improvements in the computer technology supporting such scientific instruments, among other improvements).

The embodiments disclosed herein may achieve a means for identifying device errors and monitoring system health in a large laboratory environment. Additionally, among other things, various ones of the embodiments disclosed herein may provide improvements to graphical user interface (GUI) technology. For example, GUIs provided herein provide an organized view of the status of all components (e.g., devices and scientific instruments) within a support system.

Various ones of the embodiments disclosed herein may improve upon conventional approaches to achieve the technical advantages of increased throughput of performing experiments by identifying instrument errors and delaying performance of operations until the system recovers from errors and latency. Such technical advantages are not achievable by routine and conventional approaches, and all users of systems including such embodiments may benefit from these advantages (e.g., by assisting the user in the performance of a technical task, such as identifying downed instruments and failed command routes, by means of a guided human-machine interaction process). The technical features of the embodiments disclosed herein are thus decidedly unconventional in the field of laboratory communication systems, as are the combinations of the features of the embodiments disclosed herein. The computational and user interface features disclosed herein do not only involve the collection and comparison of information, but apply new analytical and technical techniques to change the operation of instrument support systems. The present disclosure thus introduces functionality that neither a conventional computing device, nor a human, could perform.

Accordingly, the embodiments of the present disclosure may serve any of a number of technical purposes, such as controlling a specific technical system or process; determining from measurements how to control a machine; optimizing load distribution in a computer network; simulating the behavior of a technical item or process; or providing a faster processing of sensor data.

In the following detailed description, reference is made to the accompanying drawings that form a part hereof wherein like numerals designate like parts throughout, and in which is shown, by way of illustration, embodiments that may be practiced. It is to be understood that other embodiments may be utilized, and structural or logical changes may be made, without departing from the scope of the present disclosure. Therefore, the following detailed description is not to be taken in a limiting sense.

Various operations may be described as multiple discrete actions or operations in turn, in a manner that is most helpful in understanding the subject matter disclosed herein. However, the order of description should not be construed as to imply that these operations are necessarily order dependent. In particular, these operations may not be performed in the order of presentation. Operations described may be performed in a different order from the described embodiment. Various additional operations may be performed, and/or described operations may be omitted in additional embodiments.

For the purposes of the present disclosure, the phrases "A and/or B" and "A or B" mean (A), (B), or (A and B). For the purposes of the present disclosure, the phrases "A, B, and/or C" and "A, B, or C" mean (A), (B), (C), (A and B), (A and C), (B and C), or (A, B, and C). Although some elements may be referred to in the singular (e.g., "a processing device"), any appropriate elements may be represented by multiple instances of that element, and vice versa. For example, a set of operations described as performed by a processing device may be implemented with different ones of the operations performed by different processing devices.

The description uses the phrases "an embodiment," "various embodiments," and "some embodiments," each of which may refer to one or more of the same or different embodiments. Furthermore, the terms "comprising," "including," "having," and the like, as used with respect to embodiments of the present disclosure, are synonymous. When used to describe a range of dimensions, the phrase "between X and Y" represents a range that includes X and Y. As used herein, an "apparatus" may refer to any individual device, collection of devices, part of a device, or collections of parts of devices. The drawings are not necessarily to scale.

FIG. 1 is a block diagram of a scientific instrument support system 100 (henceforth referred to simply as the support system 100) for performing support operations, in accordance with various embodiments. As illustrated in FIG. 1, the support system 100 includes a plurality of instrument control personal computer (ICP)s 105 connected over a communication network 120. One or more devices 110 are connected to each ICP 105. Devices 110 are physical entities that perform some function of sample preparation and/or sample analysis. For example, devices 110 may be physical devices having a serial number, a means of communicating with other external entities, and may include processors, memory, and firmware. Devices 110 may include, for example, sensors, detectors, actuators, spectrometers, spectrograms, oscilloscopes, electrometers, interferometers, and the like. The ICPs 105 may also include one or more instruments 112. Instruments 112 are logical containers that include a collection of devices 110. For example, devices 110 work together to perform operations and produce results. The logical collection of devices 110, (e.g., the instrument 112) prepares or analyzes inputs, such as blood samples. Each ICP 105 is connected to its respective device(s) 110 and may be capable of uni-directional or bi-directional communication with the connected device(s) 110. Each ICP 105 may be connected to the device(s) 110 via wired or wireless communication means and/or protocols. Each ICP 105 may transmit commands to the connected device(s) 110, receive status signals from the device(s) 110, receive measurements from the device(s) 110, and the like, as described below in more detail. The ICPs 105, the devices 110, and the instruments 112 may be more generally referred to as service components.

The support system 100 includes a database 125 and a server 115 communicatively coupled with the plurality of ICPs 105 (and with each other) through the communication network 120. In other embodiments, the plurality of ICPs 105, the server 115, and the database 125 communicate via one or more dedicated wire connections or other forms of wired or wireless electronic communication. It should be understood that the support system 100 may include fewer or additional components than those illustrated in FIG. 1. For example, the support system 100 may include fewer or more ICPs 105, multiple servers 115, multiple databases 125, or a combination thereof. In some instances, rather than including an independent database, the storage functionality of the database 125 is provided by the server 115. The components of the support system 100 may also communicate through one or more intermediary devices not illustrated in FIG. 1.

The server 115 serves as a "control hub" for the plurality of ICPs 105. For example, the server 115 communicates with each of the ICPs 105 by sending commands to the ICPs 105 to perform methods described herein over a wired connection, a wireless connection, or a combination thereof. Additionally, the server 115 receives measurements and statuses of device(s) 110 and instrument(s) 112 from their respective ICPs 105 over a wired connection, wireless connection, or a combination thereof. The database 125 stores data indicating the status of components within the support system 100. For example, the database 125 may store a current status of the device(s) 110 and instrument(s) 112, historical statuses of the device(s) 110 and instrument(s) 112, measurements recorded by the device(s) 110 and instrument(s) 112, and the like.

Figure 2A:
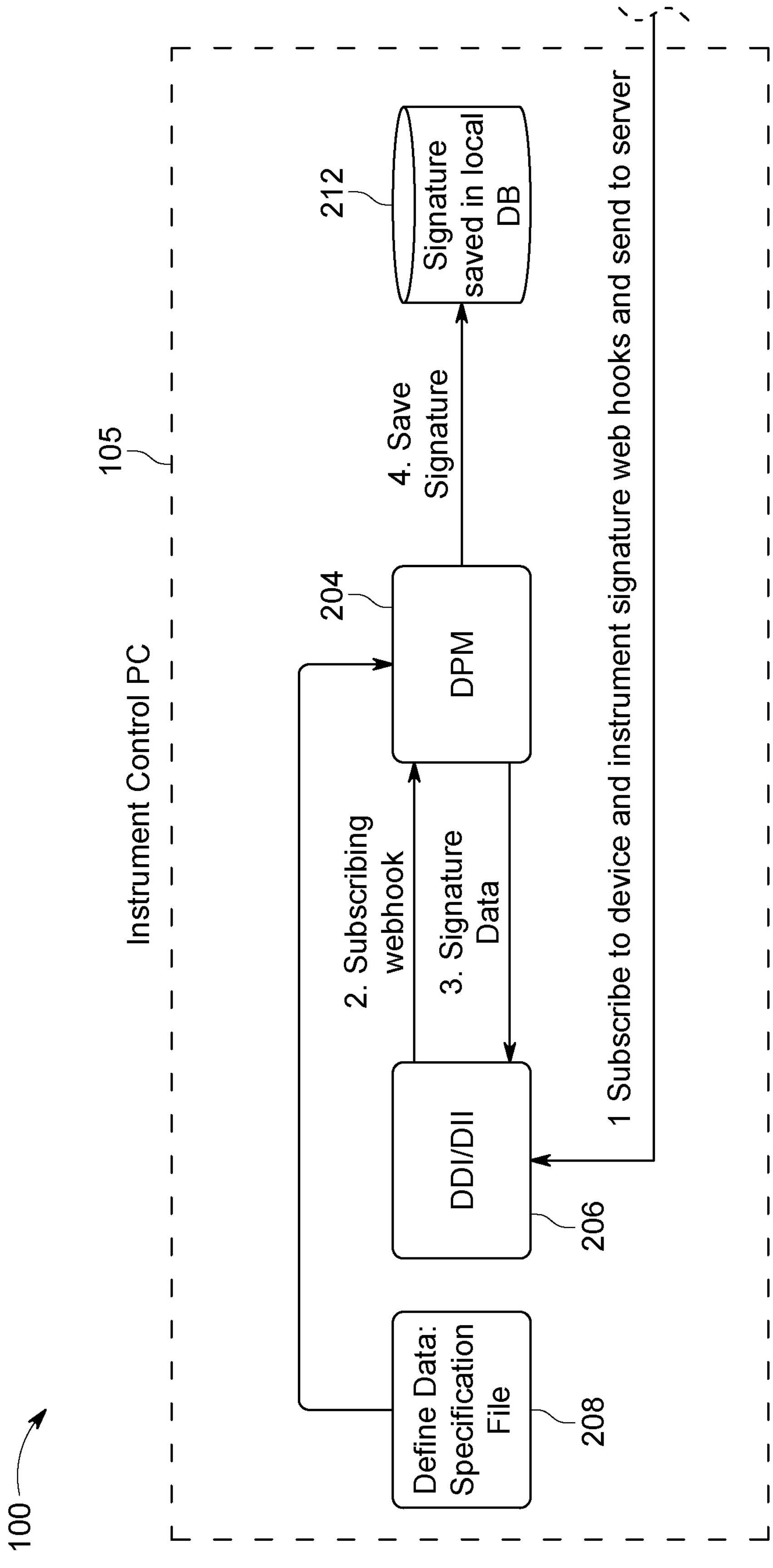
FIGS. 2A and 2B are block diagrams of an example scientific instrument support system for performing support operations, in accordance with various embodiments.
Figure 2B:
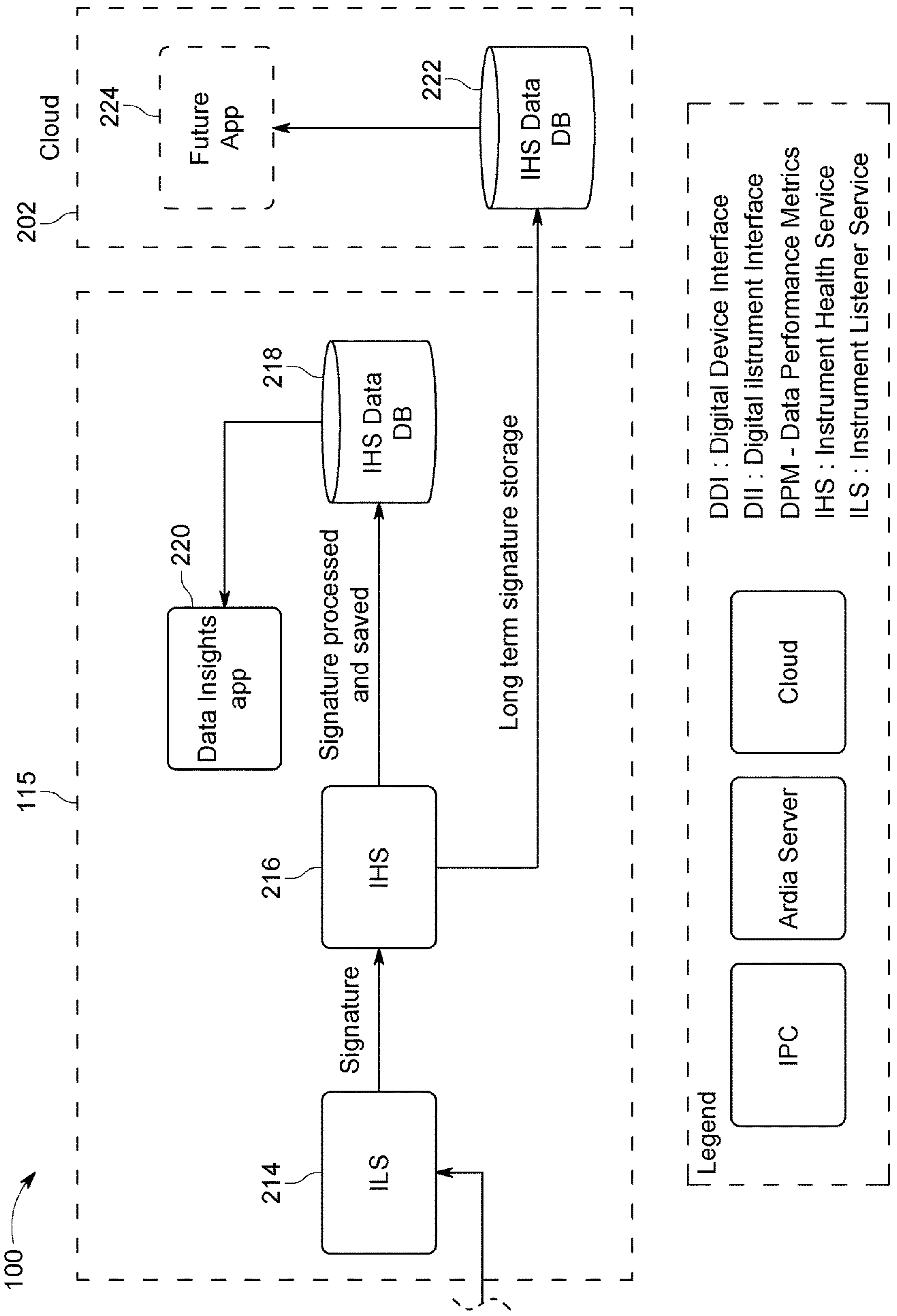

FIGS. 2A and 2B illustrate aspects of the support system 100 in more detail. In the example illustrated in FIGS. 2A and 2B, the support system 100 includes one or more ICPs 105, a server 115, and a cloud component 202. The cloud component 202, described below, is a cloud computing instance remote from the other components of the support system 100 and accessible via one or more intervening data networks. In some aspects, the server 115 may be located on a local network in physical proximity to the ICP 105 (e.g., as part of a local area network within a building or campus). In some aspects, the server 115 may be located remotely from the ICP 105 (e.g., as part of a wide area network or provided by a cloud infrastructure).

For ease of description, FIGS. 2A and 2B illustrate a single ICP 105 and server 115. However, the methods described herein are applicable to instances of the support system 100 having multiple ICPs, multiple servers, and multiple cloud instances, in various combinations. In some examples, the server 115 is configured to support one or more ICPs for a single entity (e.g., a corporate or academic organization's lab(s)). In other examples, the server 115 may support multiple groups of ICPs, where each group is operated by a distinct entity.

Figure 7:
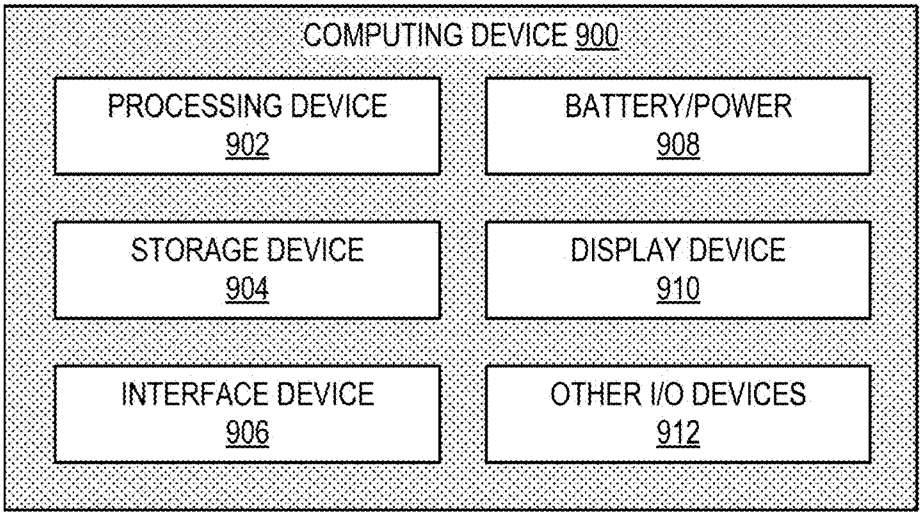
FIG. 7 is a block diagram of an example computing device that may perform some or all of the scientific instrument support methods disclosed herein, in accordance with various embodiments.

The components of the ICP 105 illustrated in FIG. 2A may be software, hardware, or combinations of both, and are executed by one or more processing devices and/or stored in one or more storage devices, each as described herein with respect to FIG. 7.

As illustrated in FIG. 2A, the ICP 105 includes a data performance metrics module (DPM) 204, which communicates with a driver module 206, to receive data manifests from one or more devices 110. As described herein, the DPM 204 processed the data manifests according to a specification file 208 to produce signature data based on a schema. As illustrated in FIG. 2A, the DPM 204 may also store the signature data in a local database 212.

The driver module 206 may implement one or more of a digital device interface and a digital instrument interface. The driver module 206 is in communication with an instrument listener service (ILS) 214, operated on the server 115. The ILS 214 and the other illustrated components of the server 115 may be software, hardware, or combinations of both, and are executed by one or more processing devices and/or stored in one or more storage devices, each as described herein with respect to FIG. 7. The ILS 214 is configured to receive request and receive signature data from one or more ICPs 105 and pass the signature data to the instrument health service (IHS) 216. The IHS 216 processes the signature data and stores it in an IHS database 218. As illustrated in FIG. 2B, the IHS database is integrated with the server 115. In some examples, the IHS database 218 is external to the server 115, and may be accessible by one or more servers in addition to the server 115.

Figure 5A:
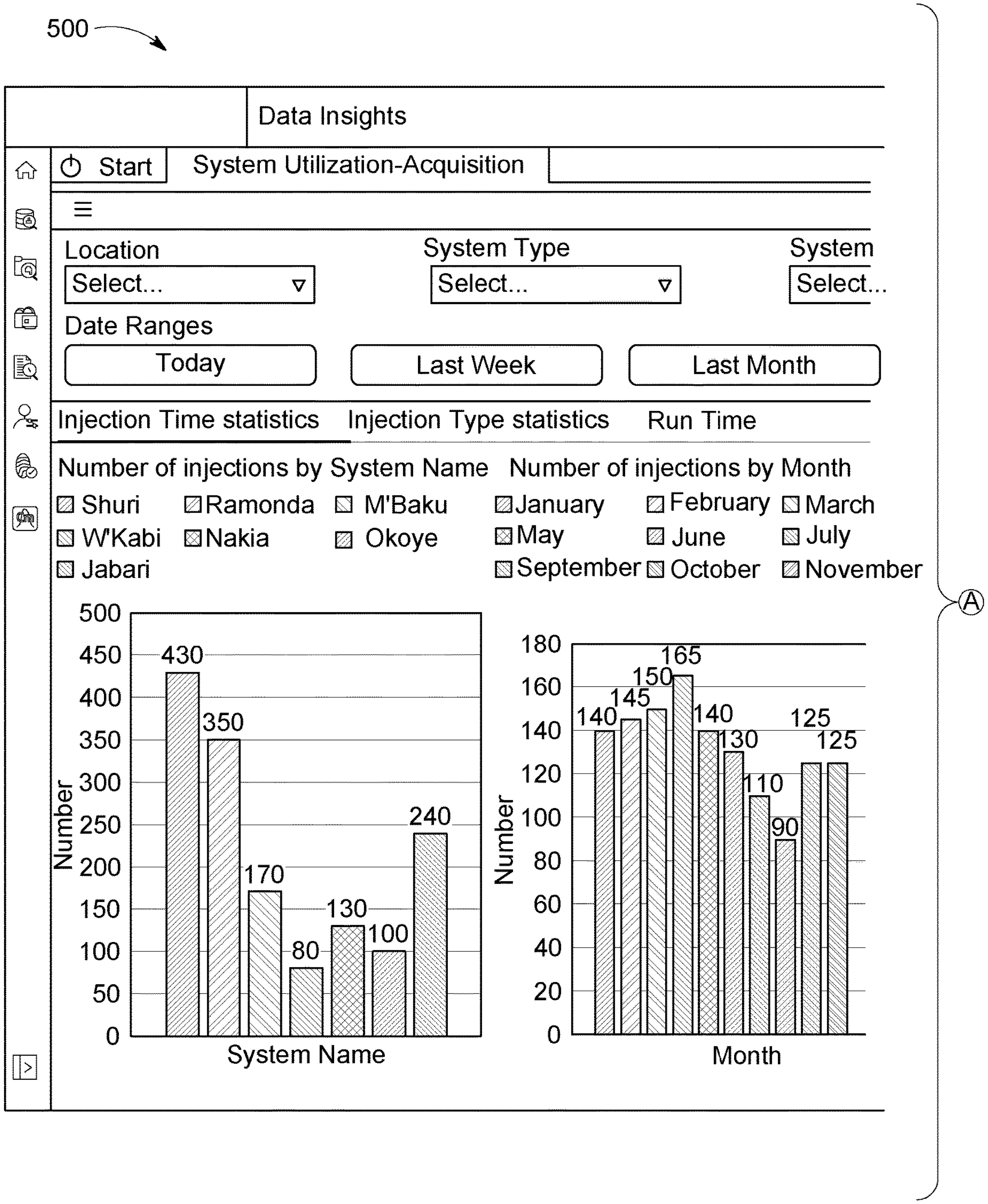
FIGS. 5A and 5B illustrate an example graphical user interface that may be used in the performance of some or all of the support methods disclosed herein, in accordance with various embodiments
Figure 5B:
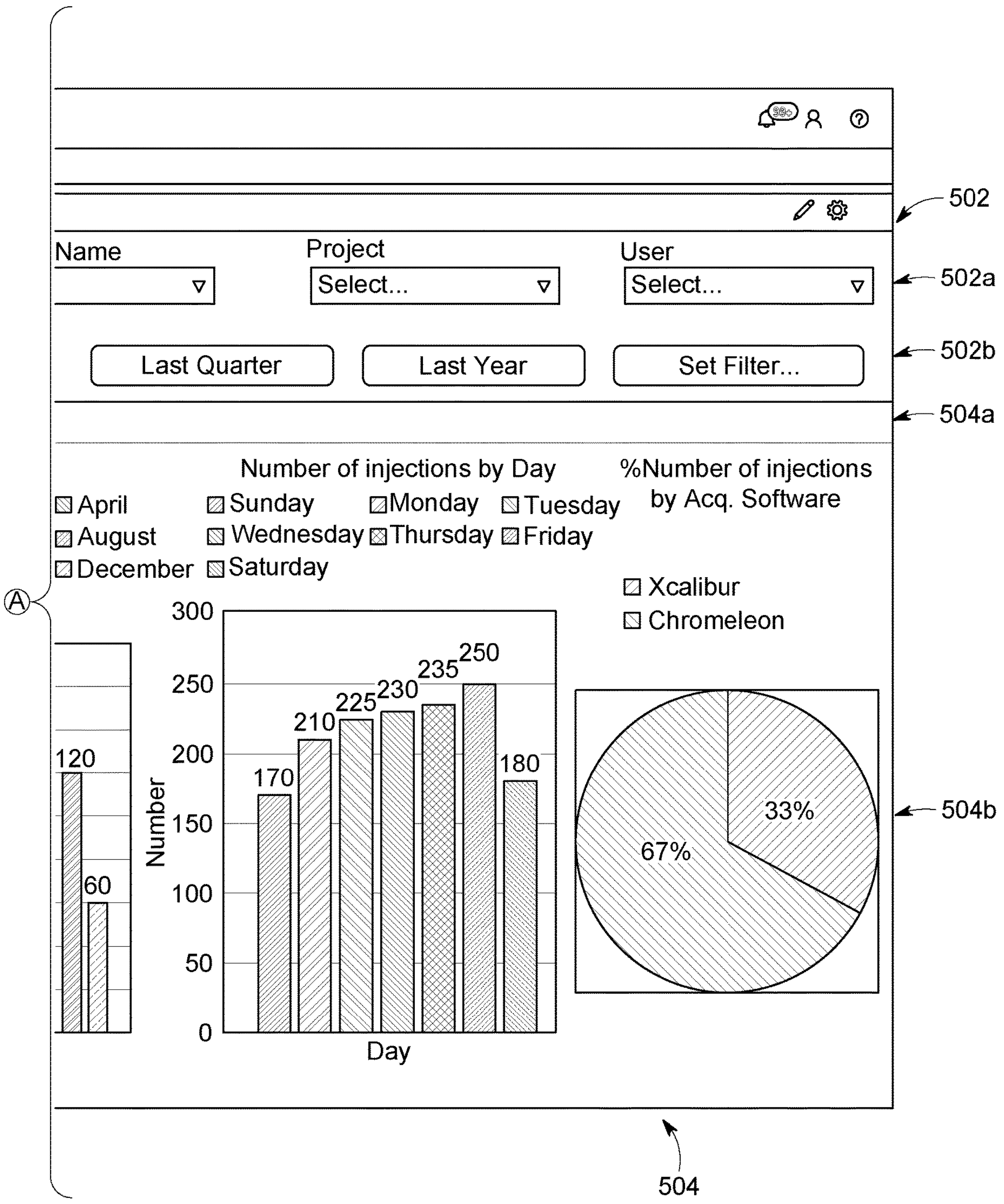

In the illustrated example, the IHS database 218 provides data to a data insights application 220, which is executed by the server 115 to provide an operator with understandable and actionable data on relevant instruments and devices (e.g., via the graphical user interface described herein with respect to FIGS. 5A and 5B).

As illustrated in FIG. 2B, the IHS 216 may also transmit the signature data to the cloud component 202. The cloud component 202 stores the signature data in a cloud database 222 and may provide access to the data via a cloud-based application 224, which operates similarly to the data insights application 220. In some aspects, the data insights application 220 provides access to a single entity, while the cloud-based application 224 provides secure access for multiple entities to their respective data.

Figure 3:
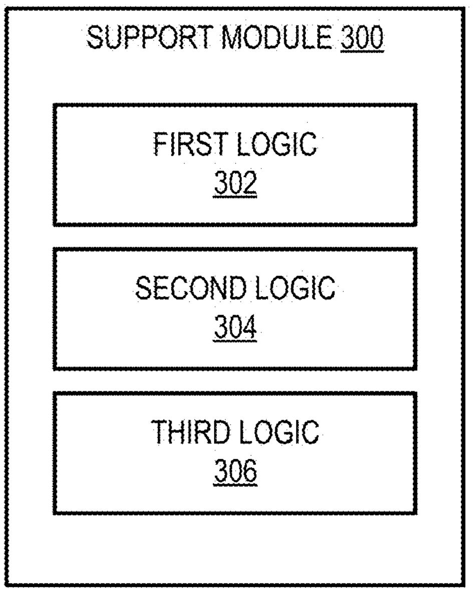
FIG. 3 is a block diagram of an example scientific instrument support module for performing support operations, in accordance with various embodiments.

FIG. 3 is a block diagram of a scientific instrument support module 300 for performing support operations, in accordance with various embodiments. The scientific instrument support module 300 may be, for example, the server 115. The scientific instrument support module 300 may be implemented by circuitry (e.g., including electrical and/or optical components), such as a programmed computing device. The logic of the scientific instrument support module 300 may be included in a single computing device or may be distributed across multiple computing devices that are in communication with each other as appropriate. Examples of computing devices that may, singly or in combination, implement the scientific instrument support module 300 are discussed herein with reference to the computing device 900 of FIG. 7, and examples of systems of interconnected computing devices, in which the scientific instrument support module 300 may be implemented across one or more of the computing devices, is discussed herein with reference to the scientific instrument support system 1000 of FIG. 8.

The scientific instrument support module 300 may include first logic 302, second logic 304, and a third logic 306. As used herein, the term "logic" may include an apparatus that is to perform a set of operations associated with the logic. For example, any of the logic elements included in the support module 300 may be implemented by one or more computing devices programmed with instructions to cause one or more processing devices of the computing devices to perform the associated set of operations. In a particular embodiment, a logic element may include one or more non-transitory computer-readable media having instructions thereon that, when executed by one or more processing devices of one or more computing devices, cause the one or more computing devices to perform the associated set of operations. As used herein, the term "module" may refer to a collection of one or more logic elements that, together, perform a function associated with the module. Different ones of the logic elements in a module may take the same form or may take different forms. For example, some logic in a module may be implemented by a programmed general-purpose processing device, while other logic in a module may be implemented by an application-specific integrated circuit (ASIC). In another example, different ones of the logic elements in a module may be associated with different sets of instructions executed by one or more processing devices. A module may not include all of the logic elements depicted in the associated drawing; for example, a module may include a subset of the logic elements depicted in the associated drawing when that module is to perform a subset of the operations discussed herein with reference to that module.

The first logic 302 may include an apparatus for sending to a device driver (e.g., the device module 206) requests to subscribe to events from a device driver. Events relate to signature data, which is transmitted from the device driver to the first logic 302. In some aspects, the requests may identity events for specific devices or instruments. For example, as illustrated in FIG. 2B, the server 115 implements an ILS 214, which may send (e.g., using a REST API) subscribing webhook that makes the subscription requests. Requests may include a device identifier may be used identify a specific device, group of devices, or instrument, for which data is requested. Requests may include a signature identifier may include information identifying a specification file (e.g., the specification file 208) for use in processing the requested data. A specification file defines what and how information is to be gathered for a family of instruments. In some examples, a specification file is a JavaScript Object Notation (JSON) file containing the attributes (for an instrument of family of instruments) that an operator wants to collect at the frequency the operator wants to collect them.

The first logic 302 also receives from the device driver, signature data events based on the event subscriptions. Signature data events may include generate signature events. A generated signature event is a request to generate a signature data with a specified signature identifier. The first logic 302 generates signature data responsive to receiving the generate signature event. As described below with respect to the method 600, the signature data is produced by the DPM 204 using the specification file 208. The first logic transmits the signature data to the second logic 304, which may include an apparatus for receiving the signature data from the first logic 302. The second logic 304 processes the signature data. For example, the data may be parsed, chunked, binned, normalized, parsed, or the like to prepare it for subsequent use (e.g., by the data insights application 220). The second logic 304 writes the processed signature data to an instrument health database (e.g., the IHS database 218) and transmits the signature data to a cloud-based database (e.g., the cloud database 222). In some examples, the second logic 304 transmits the original signature data to the cloud-based database. In another example, the second logic 304 transmits the processed signature data to the cloud-based database, or it transmits both the original and the processed signature data.

The third logic 306 may include an apparatus for presenting a graphical user interface based on the signature data (e.g., in some instances, the processed signature data). For example, the server 115 implements a graphical user interface 500 via the data insights application 220. The graphical user interface 500 may display the results of data analysis (e.g., the results of analyzing the signature data and/or other data). For example, the data insights application 220 may display the statuses of components within the support system 100.

As noted, data signatures may be a text-based format for storing data retrieved from devices and instruments. Data signatures utilize a Resource Description Framework (RDF) for storing instrument health data. Data signatures are produced based on a specification file and may be formatted according to one of many schemas.

For example, FIGS. 4A-4C illustrate an example of a device declaration signature 400. The example signature 400 defines an instrument (a Mass Spectrometer) and all of the devices that make up the instrument, providing unique identifiers for each. This declaration may be used by the support system 100 for processing subsequent data received from the mass spectrometer or may be used by the data insights application 220.

In another example, FIG. 4D illustrates an example of a state signature 402. A state signature may be used to identify a current state for a device or to indicate a state change for a device, as illustrated in FIG. 4D.

In another example, FIG. 4E illustrates an example of an observation signature 404. An observation signature provides aggregation data for a specified time period. In the illustrated example, an observation of the vacuum pressure for a pump is presented as a min/max/mean over a 24 hour period.

In another example, FIG. 4F illustrates an example of a usage signature 406. A usage signature indicates how long a particular device function was being used. In the illustrated example, a heated electrospray ionization source was used for 82,800 seconds.

Other examples of signature schema include a setting schema (e.g., a configuration setting for a device), an activity schema (e.g., what a device is doing), and an event schema (e.g., an indication that a process has begun or stopped for the device).

FIGS. 5A and 5B depict an example GUI 500 that may be used in the performance of some, or all of the support methods disclosed herein, in accordance with various embodiments. As noted above, the GUI 500 may be provided on a display device (e.g., the display device 910 discussed herein with reference to FIG. 7) of a computing device (e.g., the computing device 900 discussed herein with reference to FIG. 7) of a scientific instrument support system (e.g., the scientific instrument support system 1000 discussed herein with reference to FIG. 8) by the data insights application 220. A user may interact with the GUI 500 using any suitable input device (e.g., any of the input devices included in the other I/O devices 912 discussed herein with reference to FIG. 7) and input technique (e.g., movement of a cursor, motion capture, facial recognition, gesture detection, voice recognition, actuation of buttons, etc.).

The GUI 500 may include a settings region 502 and a data display region 504. The particular number and arrangement of regions depicted in FIGS. 5A and 5B is simply illustrative, and any number and arrangement of regions, including any desired features, may be included in a GUI 500.

The settings region 502 allows an operator to select and filter the data for display in the data display region 504. The settings region may include a type subregion 502*a* and a date select subregion 502*b*. The type subregion 502*a* allows an operator to select and/or filter the data based on, for example, a location, a system type, a system name, a project, a user, or combinations thereof. The data select subregion 502*b* allows an operator to filter the data to be displayed based on a range of dates for the data.

The data display region 504 displays data in a data display subregion 504*b*. The data display region 504 may display data generated by a scientific instrument (e.g., the scientific instrument 1010 discussed herein with reference to FIG. 8), or may display data related to the status of components within the support system 100. For example, the data display region 502 may display a table or chart providing the status of components within the support system 100, an example of which is shown in FIGS. 5A and 5B. In some examples, the data display region 504 may include tabs 504*a*, which allow an operator to select from one of several data sets to display in the data display subregion 504*b*.

Figure 6:
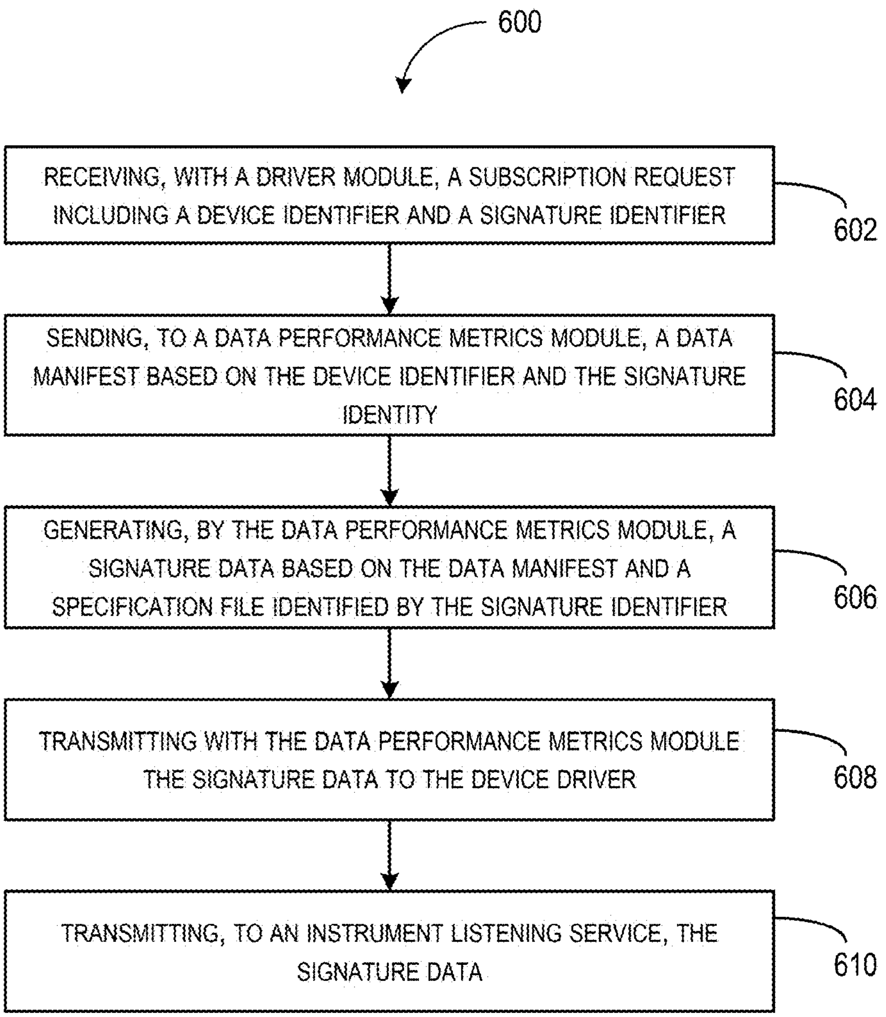
FIG. 6 is a flow diagram of an example method of performing support operations, in accordance with various embodiments.

FIG. 6 is a flow diagram of a method 600 of performing support operations, in accordance with various embodiments. Although the operations of the method 600 may be illustrated with reference to particular embodiments disclosed herein (e.g., the scientific instrument support module 300 discussed herein with reference to FIG. 6, the GUI 500 discussed herein with reference to FIGS. 5A and 5B, the computing devices 900 discussed herein with reference to FIG. 7, and/or the scientific instrument support system 1000 discussed herein with reference to FIG. 8), the method 600 may be used in any suitable setting to perform any suitable support operations. Operations are illustrated once each and in a particular order in FIG. 6, but the operations may be reordered and/or repeated as desired and appropriate (e.g., different operations performed may be performed in parallel, as suitable).

At block 602, the method 600 includes receiving, with the driver module 206, a subscription request including a device identifier and a signature identifier. The device identifier identifies one or more devices and/or instruments, for which data is to be collected. The signature identifier identifies information identifying a specification file, which defines what and how information is to be gathered for a family of instruments associated with the device identifier.

At block 604 the method 600 includes sending to a data performance metrics module (e.g., the DPM 204, a data manifest based on the device identifier and the signature identifier. A data manifest is produced by a device and may include key value pairs for some, or all of the data produced by the device. In some cases, the data is sent to the DPM 204 using a push method (e.g., sending data periodically as it is reported from the devices). In other cases, the data is sent to the DPM 204 in answer to a pull request from the DPM 204.

The data manifest is a large collection of raw data. Accordingly, at block 606, the method 600 includes generating, with the data performance metrics module, signature data from the manifest data. The signature data is a reduced set of the manifest data, formatted in a specific way based on the data manifest and a specification file identified by the signature identifier. For example, the DPM 204 may parse the manifest to extract and/or summarize the data called for in the specification. In some instances, the signature identifier further specifies a signature schema. A signature schema specifies a type for the signature data, as described in part with respect to FIG. 4A-D. In such instances, the signature data is generated based on the signature schema.

At block 608, the method 600 includes transmitting (e.g., with the DPM 204) the signature data to the driver module 206. This may be done using a webhook. In some examples, in addition to returning the signature data to the driver module, the DPM 204 stores the signature data on a local database (e.g., the database 212).

At block 610, the method 600 includes transmitting, to an instrument listening service (e.g., the ILS 214), the signature data. For example, the driver module 206 may send the signature data using a REST API.

FIG. 7 is a block diagram of a computing device 900 that may perform some or all of the scientific instrument support methods disclosed herein, in accordance with various embodiments. In some embodiments, the scientific instrument support module 300 (for example, the server 115) may be implemented by a single computing device 900 or by multiple computing devices 900. Further, as discussed below, a computing device 900 (or multiple computing devices 900) that implements the scientific instrument support module 300 may be part of one or more of the scientific instrument 1010, the user local computing device 1020, the service local computing device 1030, or the remote computing device 1040 of FIG. 8.

The computing device 900 of FIG. 7 is illustrated as having a number of components, but any one or more of these components may be omitted or duplicated, as suitable for the application and setting. In some embodiments, some or all of the components included in the computing device 900 may be attached to one or more motherboards and enclosed in a housing (e.g., including plastic, metal, and/or other materials). In some embodiments, some these components may be fabricated onto a single system-on-a-chip (SoC) (e.g., an SoC may include one or more processing devices 902 and one or more storage devices 904). Additionally, in various embodiments, the computing device 900 may not include one or more of the components illustrated in FIG. 7, but may include interface circuitry (not shown) for coupling to the one or more components using any suitable interface (e.g., a Universal Serial Bus (USB) interface, a High-Definition Multimedia Interface (HDMI) interface, a Controller Area Network (CAN) interface, a Serial Peripheral Interface (SPI) interface, an Ethernet interface, a wireless interface, or any other appropriate interface). For example, the computing device 900 may not include a display device 910, but may include display device interface circuitry (e.g., a connector and driver circuitry) to which a display device 910 may be coupled.

The computing device 900 may include a processing device 902 (e.g., one or more processing devices). As used herein, the term "processing device" may refer to any device or portion of a device that processes electronic data from registers and/or memory to transform that electronic data into other electronic data that may be stored in registers and/or memory. The processing device 902 may include one or more digital signal processors (DSPs), application-specific integrated circuits (ASICs), central processing units (CPUs), graphics processing units (GPUs), cryptoprocessors (specialized processors that execute cryptographic algorithms within hardware), server processors, or any other suitable processing devices.

The computing device 900 may include a storage device 904 (e.g., one or more storage devices). The storage device 904 may include one or more memory devices such as random access memory (RAM) (e.g., static RAM (SRAM) devices, magnetic RAM (MRAM) devices, dynamic RAM (DRAM) devices, resistive RAM (RRAM) devices, or conductive-bridging RAM (CBRAM) devices), hard drive-based memory devices, solid-state memory devices, networked drives, cloud drives, or any combination of memory devices. In some embodiments, the storage device 904 may include memory that shares a die with a processing device 902. In such an embodiment, the memory may be used as cache memory and may include embedded dynamic random-access memory (eDRAM) or spin transfer torque magnetic random-access memory (STT-MRAM), for example. In some embodiments, the storage device 904 may include non-transitory computer readable media having instructions thereon that, when executed by one or more processing devices (e.g., the processing device 902), cause the computing device 900 to perform any appropriate ones of or portions of the methods disclosed herein.

The computing device 900 may include an interface device 906 (e.g., one or more interface devices 906). The interface device 906 may include one or more communication chips, connectors, and/or other hardware and software to govern communications between the computing device 900 and other computing devices. For example, the interface device 906 may include circuitry for managing wireless communications for the transfer of data to and from the computing device 900. The term "wireless" and its derivatives may be used to describe circuits, devices, systems, methods, techniques, communications channels, etc., that may communicate data through the use of modulated electromagnetic radiation through a nonsolid medium. The term does not imply that the associated devices do not contain any wires, although in some embodiments they might not. Circuitry included in the interface device 4006 for managing wireless communications may implement any of a number of wireless standards or protocols, including but not limited to Institute for Electrical and Electronic Engineers (IEEE) standards including Wi-Fi (IEEE 802.11 family), IEEE 802.16 standards (e.g., IEEE 802.16-2005 Amendment), Long-Term Evolution (LTE) project along with any amendments, updates, and/or revisions (e.g., advanced LTE project, ultra mobile broadband (UMB) project (also referred to as "3GPP2"), etc.). In some embodiments, circuitry included in the interface device 4006 for managing wireless communications may operate in accordance with a Global System for Mobile Communication (GSM), General Packet Radio Service (GPRS), Universal Mobile Telecommunications System (UMTS), High Speed Packet Access (HSPA), Evolved HSPA (E-HSPA), or LTE network. In some embodiments, circuitry included in the interface device 4006 for managing wireless communications may operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). In some embodiments, circuitry included in the interface device 4006 for managing wireless communications may operate in accordance with Code Division Multiple Access (CDMA), Time Division Multiple Access (TDMA), Digital Enhanced Cordless Telecommunications (DECT), Evolution-Data Optimized (EV-DO), and derivatives thereof, as well as any other wireless protocols that are designated as 3G, 4G, 5G, and beyond. In some embodiments, the interface device 906 may include one or more antennas (e.g., one or more antenna arrays) to receipt and/or transmission of wireless communications.

In some embodiments, the interface device 906 may include circuitry for managing wired communications, such as electrical, optical, or any other suitable communication protocols. For example, the interface device 906 may include circuitry to support communications in accordance with Ethernet technologies. In some embodiments, the interface device 906 may support both wireless and wired communication, and/or may support multiple wired communication protocols and/or multiple wireless communication protocols. For example, a first set of circuitry of the interface device 906 may be dedicated to shorter-range wireless communications such as Wi-Fi or Bluetooth, and a second set of circuitry of the interface device 906 may be dedicated to longer-range wireless communications such as global positioning system (GPS), EDGE, GPRS, CDMA, WiMAX, LTE, EV-DO, or others. In some embodiments, a first set of circuitry of the interface device 906 may be dedicated to wireless communications, and a second set of circuitry of the interface device 906 may be dedicated to wired communications.

The computing device 900 may include battery/power circuitry 908. The battery/power circuitry 908 may include one or more energy storage devices (e.g., batteries or capacitors) and/or circuitry for coupling components of the computing device 900 to an energy source separate from the computing device 900 (e.g., AC line power).

The computing device 900 may include a display device 910 (e.g., multiple display devices). The display device 910 may include any visual indicators, such as a heads-up display, a computer monitor, a projector, a touchscreen display, a liquid crystal display (LCD), a light-emitting diode display, or a flat panel display.

The computing device 900 may include other input/output (I/O) devices 912. The other I/O devices 912 may include one or more audio output devices (e.g., speakers, headsets, earbuds, alarms, etc.), one or more audio input devices (e.g., microphones or microphone arrays), location devices (e.g., GPS devices in communication with a satellite-based system to receive a location of the computing device 900, as known in the art), audio codecs, video codecs, printers, sensors (e.g., thermocouples or other temperature sensors, humidity sensors, pressure sensors, vibration sensors, accelerometers, gyroscopes, etc.), image capture devices such as cameras, keyboards, cursor control devices such as a mouse, a stylus, a trackball, or a touchpad, bar code readers, Quick Response (QR) code readers, or radio frequency identification (RFID) readers, for example.

The computing device 900 may have any suitable form factor for its application and setting, such as a handheld or mobile computing device (e.g., a cell phone, a smart phone, a mobile internet device, a tablet computer, a laptop computer, a personal digital assistant (PDA), etc.), a desktop computing device, or a server computing device or other networked computing component.

Figure 8:
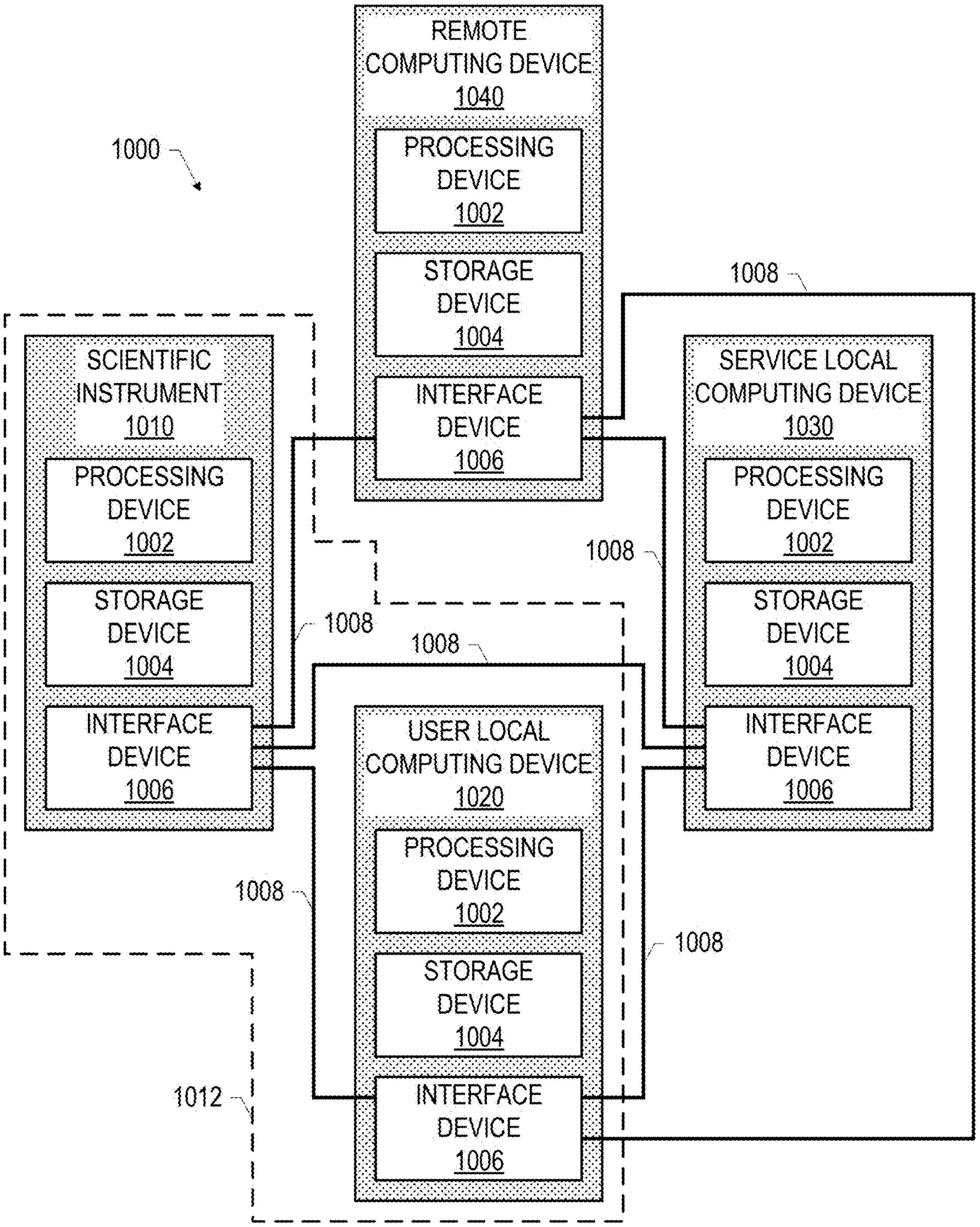
FIG. 8 is a block diagram of another example scientific instrument support system in which some or all of the scientific instrument support methods disclosed herein may be performed, in accordance with various embodiments.

One or more computing devices implementing any of the scientific instrument support modules or methods disclosed herein may be part of a scientific instrument support system. FIG. 8 is a block diagram of an example scientific instrument support system 1000 in which some or all of the scientific instrument support methods disclosed herein may be performed, in accordance with various embodiments. The scientific instrument support modules and methods disclosed herein (e.g., the scientific instrument support module 300 of FIG. 3 and the method 600 of FIG. 6) may be implemented by one or more of the scientific instrument 1010, the user local computing device 1020, the service local computing device 1030, or the remote computing device 1040 of the scientific instrument support system 1000. The scientific instrument support system 1000 may be a system that operates within the support system 100 of FIG. 1, the scientific support system 200 of FIGS. 2A and 2B, or may alternatively be a separate system that implements the support methods described herein. For example, the scientific instrument 1010 may be an example instrument 112, and the operations of the ICP 105 and the server 115 may be separated among the user local computing device 1020, the service local computing device 1030, and the remote computing device 1040.

Any of the scientific instrument 1010, the user local computing device 1020, the service local computing device 1030, or the remote computing device 1040 may include any of the embodiments of the computing device 900 discussed herein with reference to FIG. 7, and any of the scientific instrument 1010, the user local computing device 1020, the service local computing device 1030, or the remote computing device 1040 may take the form of any appropriate ones of the embodiments of the computing device 900 discussed herein with reference to FIG. 7.

The scientific instrument 1010, the user local computing device 1020, the service local computing device 1030, or the remote computing device 1040 may each include a processing device 1002, a storage device 1004, and an interface device 1006. The processing device 1002 may take any suitable form, including the form of any of the processing devices 902 discussed herein with reference to FIG. 7, and the processing devices 1002 included in different ones of the scientific instrument 1010, the user local computing device 1020, the service local computing device 1030, or the remote computing device 1040 may take the same form or different forms. The storage device 1004 may take any suitable form, including the form of any of the storage devices 1004 discussed herein with reference to FIG. 7, and the storage devices 1004 included in different ones of the scientific instrument 1010, the user local computing device 1020, the service local computing device 1030, or the remote computing device 1040 may take the same form or different forms. The interface device 1006 may take any suitable form, including the form of any of the interface devices 906 discussed herein with reference to FIG. 7, and the interface devices 1006 included in different ones of the scientific instrument 1010, the user local computing device 1020, the service local computing device 1030, or the remote computing device 1040 may take the same form or different forms.

The scientific instrument 1010, the user local computing device 1020, the service local computing device 1030, and the remote computing device 1040 may be in communication with other elements of the scientific instrument support system 1000 via communication pathways 1008. The communication pathways 1008 may communicatively couple the interface devices 1006 of different ones of the elements of the scientific instrument support system 1000, as shown, and may be wired or wireless communication pathways (e.g., in accordance with any of the communication techniques discussed herein with reference to the interface devices 906 of the computing device 900 of FIG. 7). The particular scientific instrument support system 1000 depicted in FIG. 8 includes communication pathways between each pair of the scientific instrument 1010, the user local computing device 1020, the service local computing device 1030, and the remote computing device 1040, but this "fully connected" implementation is simply illustrative, and in various embodiments, various ones of the communication pathways 1008 may be absent. For example, in some embodiments, a service local computing device 1030 may not have a direct communication pathway 1008 between its interface device 1006 and the interface device 1006 of the scientific instrument 1010, but may instead communicate with the scientific instrument 1010 via the communication pathway 1008 between the service local computing device 1030 and the user local computing device 1020 and the communication pathway 1008 between the user local computing device 1020 and the scientific instrument 1010.

The user local computing device 1020 may be a computing device (e.g., in accordance with any of the embodiments of the computing device 900 discussed herein) that is local to a user of the scientific instrument 1010. In some embodiments, the user local computing device 1020 may also be local to the scientific instrument 1010, but this need not be the case; for example, a user local computing device 1020 that is in a user's home or office may be remote from, but in communication with, the scientific instrument 1010 so that the user may use the user local computing device 1020 to control and/or access data from the scientific instrument 1010. In some embodiments, the user local computing device 1020 may be a laptop, smartphone, or tablet device. In some embodiments the user local computing device 1020 may be a portable computing device. In some embodiments, the user local computing device 5020 may be an ICP 105.

The service local computing device 1030 may be a computing device (e.g., in accordance with any of the embodiments of the computing device 900 discussed herein) that is local to an entity that services the scientific instrument 1010. For example, the service local computing device 1030 may be local to a manufacturer of the scientific instrument 1010 or to a third-party service company. In some embodiments, the service local computing device 1030 may communicate with the scientific instrument 1010, the user local computing device 1020, and/or the remote computing device 1040 (e.g., via a direct communication pathway 1008 or via multiple "indirect" communication pathways 1008, as discussed above) to receive data regarding the operation of the scientific instrument 1010, the user local computing device 1020, and/or the remote computing device 1040 (e.g., the results of self-tests of the scientific instrument 1010, calibration coefficients used by the scientific instrument 1010, the measurements of sensors associated with the scientific instrument 1010, etc.). In some embodiments, the service local computing device 1030 may communicate with the scientific instrument 1010, the user local computing device 1020, and/or the remote computing device 1040 (e.g., via a direct communication pathway 1008 or via multiple "indirect" communication pathways 1008, as discussed above) to transmit data to the scientific instrument 1010, the user local computing device 1020, and/or the remote computing device 1040 (e.g., to update programmed instructions, such as firmware, in the scientific instrument 1010, to initiate the performance of test or calibration sequences in the scientific instrument 1010, to update programmed instructions, such as software, in the user local computing device 1020 or the remote computing device 1040, etc.). A user of the scientific instrument 1010 may utilize the scientific instrument 1010 or the user local computing device 1020 to communicate with the service local computing device 1030 to report a problem with the scientific instrument 1010 or the user local computing device 1020, to request a visit from a technician to improve the operation of the scientific instrument 1010, to order consumables or replacement parts associated with the scientific instrument 1010, or for other purposes.

The remote computing device 1040 may be a computing device (e.g., in accordance with any of the embodiments of the computing device 900 discussed herein) that is remote from the scientific instrument 1010 and/or from the user local computing device 1020. In some embodiments, the remote computing device 1040 may be included in a datacenter or other large-scale server environment. In some embodiments, the remote computing device 1040 may include network-attached storage (e.g., as part of the storage device 1004). The remote computing device 1040 may store data generated by the scientific instrument 1010, perform analyses of the data generated by the scientific instrument 1010 (e.g., in accordance with programmed instructions), facilitate communication between the user local computing device 1020 and the scientific instrument 1010, and/or facilitate communication between the service local computing device 1030 and the scientific instrument 1010. The remote computing device may be the server 115. In some embodiments, operations of the server 115 are split between the remote computing device 1040 and the service local computing device 1030.

In some embodiments, one or more of the elements of the scientific instrument support system 1000 illustrated in FIG. 8 may not be present. Further, in some embodiments, multiple ones of various ones of the elements of the scientific instrument support system 1000 of FIG. 8 may be present. For example, a scientific instrument support system 1000 may include multiple user local computing devices 1020 (e.g., different user local computing devices 1020 associated with different users or in different locations). In another example, a scientific instrument support system 1000 may include multiple scientific instruments 1010, all in communication with service local computing device 1030 and/or a remote computing device 1040; in such an embodiment, the service local computing device 1030 may monitor these multiple scientific instruments 1010, and the service local computing device 1030 may cause updates or other information may be "broadcast" to multiple scientific instruments 1010 at the same time. Different ones of the scientific instruments 1010 in a scientific instrument support system 1000 may be located close to one another (e.g., in the same room) or farther from one another (e.g., on different floors of a building, in different buildings, in different cities, etc.). In some embodiments, a scientific instrument 1010 may be connected to an Internet-of-Things (IoT) stack that allows for command and control of the scientific instrument 1010 through a web-based application, a virtual or augmented reality application, a mobile application, and/or a desktop application. Any of these applications may be accessed by a user operating the user local computing device 1020 in communication with the scientific instrument 1010 by the intervening remote computing device 1040. In some embodiments, a scientific instrument 1010 may be sold by the manufacturer along with one or more associated user local computing devices 1020 as part of a local scientific instrument computing unit 1012.

In some embodiments, different ones of the scientific instruments 1010 included in a scientific instrument support system 1000 may be different types of scientific instruments 1010; for example, one scientific instrument 1010 may be a spectrometer, while another scientific instrument 1010 may be an interferometer. In some such embodiments, the remote computing device 1040 and/or the user local computing device 1020 may combine data from different types of scientific instruments 1010 included in a scientific instrument support system 1000.

The following paragraphs provide various examples of the embodiments disclosed herein.

Example 1. A scientific instrument support apparatus, comprising: a first logic to: subscribe to events from a device driver; receive from the device driver, signature data events based on the event subscriptions, the signature data events including a generated signature event; and responsive to receiving the generate signature event, generate a signature data with a specified signature identifier; and transmit the signature data to a second logic; a second logic to: receive the signature data from the first logic; process the signature data; write the processed signature data to an instrument health database; and transmit the signature data to a cloud-based database; and a third logic to present a graphical user interface based on the processed signature data.

Example 2. The scientific instrument support apparatus of example 1, wherein the first logic, the second logic, and the third logic are implemented by a common computing device.

Example 3. The scientific instrument support apparatus of any one of examples 1 and 2, wherein at least one of the first logic, the second logic, and the third logic are implemented by a computing device remote from a scientific instrument.

Example 4. The scientific instrument support apparatus of any one of examples 1 to 3, wherein the specified signature identifier indicates a specification file to be used by the device driver to produce the signature data.

Example 5. The scientific instrument support apparatus of example 4, wherein the specification file is applied to a data manifest to produce the signature data.

Example 6. The scientific instrument support apparatus of example 4, wherein the specification file is a JSON file.

Example 7. The scientific instrument support apparatus of any one of examples 1 to 6, wherein the signature data is formatted according to a signature schema selected from a group consisting of a device declaration schema, a state schema, an observation schema, a usage schema, a setting schema, an activity schema, and an event schema.

Example 8. The scientific instrument support apparatus of any one of examples 1 to 7, wherein subscribing for events from a device driver includes transmitting a subscribing webhook.

Example 9. The scientific instrument support apparatus of any one of examples 1 to 8, wherein the first logic implements a REST API.

Example 10. A method for scientific instrument support, comprising: receiving, with a driver module, a subscription request including a device identifier and a signature identifier; sending, to a data performance metrics module, a data manifest based on the device identifier and the signature identifier; generating, by the data performance metrics module, a signature data based on the data manifest and a specification file identified by the signature identifier; transmitting with the data performance metrics module the signature data to the driver module; and transmitting, to an instrument listening service, the processed signature data.

Example 11. The method of example 10, further comprising: receiving, with the instrument listening service, the signature data; transmitting the signature data to an instrument health service; processing, by instrument health service, the signature data to generate processed signature data; and storing the processed signature data in a database.

Example 12. The method of example 11, further comprising: transmitting, by instrument health service, the signature data to a cloud-based platform.

Example 13. The method of example 12, further comprising: presenting the data to a user via a graphical user interface.

Example 14. The method of any of examples 10 to 13, further comprising: storing, with the data performance metrics module, the signature data on a local database.

Example 15. The method of any of examples 10 to 14, wherein: the signature identifier further specifies a signature schema; and generating the signature data is further based on the signature schema.

Example 16. The method of example 15, wherein the signature schema is one selected from a group consisting of a device declaration schema, a state schema, an observation schema, a usage schema, a setting schema, an activity schema, and an event schema.

Example 17. The method of any of examples 10 to 16, wherein the subscription request includes a subscribing webhook.

Example 18. The method of any of examples 10 to 17, wherein the instrument listening service implements a REST API.

Example 19. The method of any of examples 10 to 18, wherein sending the data manifest to the data performance metrics module is performed as part of either a push action initiated by the driver module or in response to a pull action initiated by the data performance metrics module.

Example 20. One or more non-transitory computer readable media having instructions thereon that, when executed by one or more processing devices of a scientific instrument support apparatus, cause the scientific instrument support apparatus to perform the method of any of examples 10-19.

The invention claimed is:

1. A scientific instrument support apparatus, comprising:

a first logic to:

subscribe to events from a device driver;

receive from the device driver, signature data events based on event subscriptions, the signature data events including a generated signature event; and responsive to receiving the generated signature event, generate a signature data with a specified signature identifier, wherein the signature data is formatted according to a Resource Description Framework (RDF); and wherein the specified signature identifier indicates a specification file that defines what and how information is to be gathered for a family of instruments; and transmit the signature data to a second logic; the second logic to:

receive the signature data from the first logic;

process the signature data;

write the processed signature data to an instrument health database; and transmit the signature data to a cloud-based database; and a third logic to present a graphical user interface based on the processed signature data.

2. The scientific instrument support apparatus of claim 1, wherein the first logic, the second logic, and the third logic are implemented by a common computing device.

3. The scientific instrument support apparatus of claim 1, wherein at least one of the first logic, the second logic, and the third logic are implemented by a computing device remote from a scientific instrument.

4. The scientific instrument support apparatus of claim 1, wherein the specified signature identifier indicates a specification file to be used by the device driver to produce the signature data.

5. The scientific instrument support apparatus of claim 4, wherein the specification file is applied to a data manifest to produce the signature data.

6. The scientific instrument support apparatus of claim 4, wherein the specification file is a JSON file.

7. The scientific instrument support apparatus of claim 1, wherein the signature data is formatted according to a signature schema selected from a group consisting of a device declaration schema, a state schema, an observation schema, a usage schema, a setting schema, an activity schema, and an event schema.

8. The scientific instrument support apparatus of claim 1, wherein subscribing for events from a device driver includes transmitting a subscribing webhook.

9. The scientific instrument support apparatus of claim 1, wherein the first logic implements a REST API.

10. A method for scientific instrument support, comprising:

receiving, with a driver module, a subscription request including a device identifier and a signature identifier;

sending, to a data performance metrics module, a data manifest based on the device identifier and the signature identifier;

generating, by the data performance metrics module, a signature data based on the data manifest and a specification file identified by the signature identifier, wherein the specification file defines what and how information is to be gathered for a family of instruments, and wherein the signature data is formatted according to a Resource Description Framework (RDF);

transmitting with the data performance metrics module the signature data to the driver module; and transmitting, to an instrument listening service, processed signature data.

11. The method of claim 10, further comprising:

receiving, with the instrument listening service, the signature data;

transmitting the signature data to an instrument health service;

processing, by instrument health service, the signature data to generate processed signature data; and storing the processed signature data in a database.

12. The method of claim 11, further comprising:

transmitting, by instrument health service, the signature data to a cloud-based platform.

13. The method of claim 12, further comprising:

presenting the processed signature data to a user via a graphical user interface.

14. The method of claim 10, further comprising:

storing, with the data performance metrics module, the signature data on a local database.

15. The method of claim 10, wherein:

the signature identifier further specifies a signature schema; and generating the signature data is further based on the signature schema.

16. The method of claim 15, wherein the signature schema is one selected from a group consisting of a device declaration schema, a state schema, an observation schema, a usage schema, a setting schema, an activity schema, and an event schema.

17. The method of claim 10, wherein the subscription request includes a subscribing webhook.

18. The method of claim 10, wherein the instrument listening service implements a REST API.

19. The method of claim 10, wherein sending the data manifest to the data performance metrics module is performed as part of either a push action initiated by the driver module or in response to a pull action initiated by the data performance metrics module.

20. One or more non-transitory computer readable media having instructions thereon that, when executed by one or more processing devices of a scientific instrument support apparatus, cause the scientific instrument support apparatus to perform the method of any of claims 10-19.

* * * * *